# (12) United States Patent
Kawahara

(10) Patent No.: US 7,678,570 B2
(45) Date of Patent: Mar. 16, 2010

(54) HUMAN CELL STRAINS FOR PROTEIN PRODUCTION, PROVIDED BY SELECTING STRAINS WITH HIGH INTRACELLULAR PROTEIN AND MUTATING WITH CARCINOGENS

(75) Inventor: Hiroharu Kawahara, Kitakyushu (JP)

(73) Assignee: Kitakyushu Foundation for the Advancement of Industry, Science and Technology (JP)

( * ) Notice: Subject to any disclaimer, the term of this patent is extended or adjusted under 35 U.S.C. 154(b) by 0 days.

(21) Appl. No.: 10/591,521

(22) PCT Filed: Oct. 27, 2004

(86) PCT No.: PCT/JP2004/016276
§ 371 (c)(1),
(2), (4) Date: Sep. 1, 2006

(87) PCT Pub. No.: WO2005/083060
PCT Pub. Date: Sep. 9, 2005

(65) Prior Publication Data
US 2007/0196896 A1    Aug. 23, 2007

(30) Foreign Application Priority Data
Mar. 1, 2004    (JP)    ............... 2004-056551

(51) Int. Cl.
*C12N 5/08*    (2006.01)
*C12N 5/00*    (2006.01)
(52) U.S. Cl. ..................... 435/366; 435/325
(58) Field of Classification Search .............. None
See application file for complete search history.

(56) References Cited

FOREIGN PATENT DOCUMENTS

| JP | 05-310795 | 11/1993 |
|---|---|---|
| JP | 06-078759 | 3/1994 |
| JP | 06-141882 | 5/1994 |
| JP | 08-501695 | 2/1996 |
| JP | 08-163982 | 6/1996 |
| JP | 2000-506379 | 5/2000 |
| JP | 2001-500381 | 1/2001 |
| JP | 2001-511342 | 8/2001 |
| JP | 2002-051780 | 2/2002 |
| JP | 2002-058476 | 2/2002 |
| JP | 2003-509025 | 3/2003 |
| JP | 2003-274963 | 9/2003 |
| WO | WO 03/051720 | 6/2003 |
| WO | WO 03/052064 | 6/2003 |

OTHER PUBLICATIONS

Erle et al. (1991) The Journal of Biological Chemistry, vol. 266, 11009-11016.*
Kawahara et al., Establishment of a human fusion partner for making human T-T hybridomas which can grow in serum free medium, 1999, Human Antibodies, vol. 9, pp. 83-87.*
Pene et al., Role of the phosphatidyllinositol 3-kinase/Akt and mTOR/P70S6-kinase pathways in the proliferation and apoptosis in multiple myeloma., Oncogene, 2002, vol. 21, pp. 6587-6597.*
Hata et al., Establishment of a monoclonal antibody to plasma cells: a comparison with CD38 and PCA-1., Clin Exp Immunol, 1994, vol. 94, pp. 370-375.*
Karpas et al., A human myeloma cell line suitable for the generation of human monoclonal antibodies, PNAS, 2001, vol. 96, pp. 1799-1804.*
Toneguzzo et al., Electric Field-Mediated DNA Transfer: Transient and Stable Gene Expression in Human and Mouse Lymphoid Cells, Molecular and Cellular Biology, 1986, vol. 6, pp. 703-706.*
Kawahara H, Supercell: the key to producing human proteins for industrial use, Jun. 2004.

* cited by examiner

*Primary Examiner*—David J Steadman
*Assistant Examiner*—Alexander D Kim
(74) *Attorney, Agent, or Firm*—Pepper Hamilton LLP

(57) ABSTRACT

A novel human cell strain enabling the continuous production of a desired protein with high efficiency, comprising a novel human cell strain established by transforming a human cell strain whose total intracellular protein weight is 0.1 to 1 mg per 1,000,000 cells; with the novel human cell strain being further characterized in that after a gene encoding a desired protein is transfected into it, the transfected cell is subsequently cultured.

3 Claims, 3 Drawing Sheets

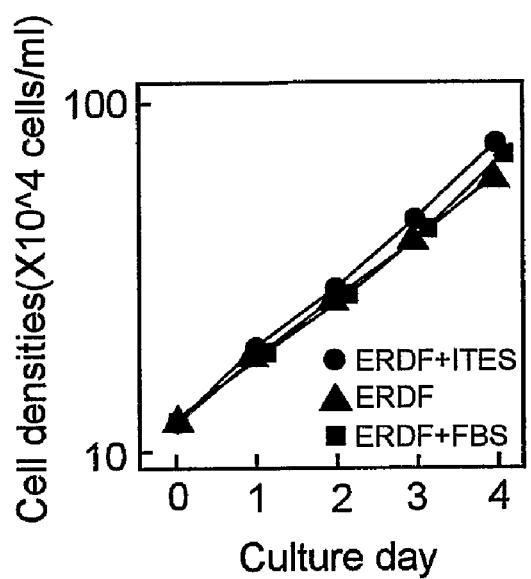
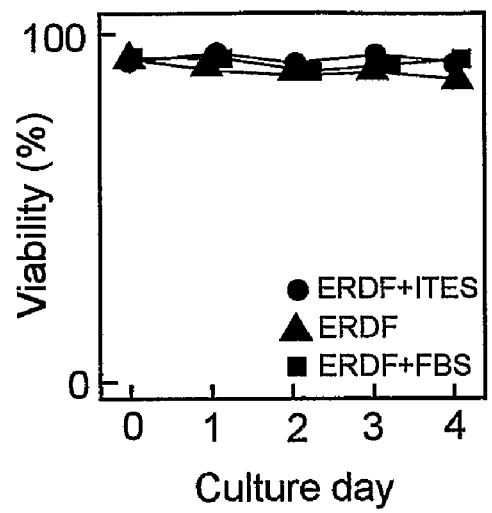
FIG. 2A
FIG. 2B

HUMAN CELL STRAINS FOR PROTEIN PRODUCTION, PROVIDED BY SELECTING STRAINS WITH HIGH INTRACELLULAR PROTEIN AND MUTATING WITH CARCINOGENS

PRIORITY FILING

This application claims foreign priority benefits from co-pending Japanese Patent Application No. 2004-056551, entitled "Protein Productive Novel Human Cell Strains, a Selection Method of the Novel Human Cell Strains, Usage of the Novel Human Cell Strains, the Protein Production and Purifying Methods Thereof, and the Pharmaceutical Compositions Utilizing the Novel Human Cell Strains", filed on Mar. 1, 2004.

FIELD OF THE INVENTION

This invention relates to an effective and economical method of producing protein that can be used for medicine or functional foods. More specifically, it relates to a human cell strain that can produce the aforementioned target protein by transfecting a gene encoding said protein, and the selection and usage thereof. Moreover, this invention relates to a method of producing protein utilizing the identified human cell strain as described above.

BACKGROUND OF THE INVENTION

In general, a protein production system utilizes microorganisms such as Ecolab to which a gene encoding desired protein is transfected, expressing said protein. However, the production of conjugated proteins (protein with sugar chain) is difficult with a microorganism due to its cellular structure. There are also undertakings for producing conjugated proteins that employ yeast and some animal cells (hamster cells). However, their problem is that the protein that is obtained has a glycosylation that is specific to the cells involved in the production, thus differing from the conjugated proteins originated from humans, which are desired for medical treatment.

At research levels, there are reports of producing protein by transfecting genes to human cells; however, the production period is at the level of approximately one month, thus being a transient result. So far, there is no example of success with a long and stable production period for industrial use.

In the other words, the following problems exist in the above-mentioned conventional methods:

First, a protein producing system utilizing prokaryotic cells such as a microorganism can produce protein with simple structure only, such as a part of the site of action (including the active center) in an enzyme. It is considered that since the intracellular protein synthetic pathways of microorganisms are different from that of higher animal cells, it is difficult to form tertiary structures of large molecular weight proteins.

In addition, in the case of conjugated proteins in which proteins are coupled with a substance other than protein such as sugar chain, since a microorganism itself does not have organs for synthesizing conjugated proteins, it is impossible to synthesize conjugated proteins in principle.

Also, unlike the case of the above-mentioned microorganism, protein production which utilizes yeast, animal cells other than that of humans, or insect cells, possesses organs to synthesize conjugated proteins within cells. Therefore, they can synthesize high levels of proteins. However, said proteins are modified with unique sugar chains derived-yeast or -heterologous cells other than that of humans. Thus it is difficult to obtain human-derived gene products.

Such problems can be solved by employing human cells (a higher animal's cells), to which a gene encoding a desired protein is transfected, and expressed. However, besides some examples of transient expression, problems remain. Such problems include the difficulty of maintaining a long-term protein production over one year, which would allow for industrial production; the loss of protein productivity within 2 months post transfection; and the smallness of expressed protein quantities.

For these problems, a method by the activation of endogenous genes in human cell strains is proposed as a way to produce conjugated protein of human origin (JP-T 2001-511342 specification (patent document 1)). However, because this technique is a production of human protein in a human cell strain by means of activating an endogenous gene, a human cell strain has to be selected according to a target protein. Thus such selection becomes an issue. Moreover, the production efficiency is unstable because it varies according to the protein to be produced. Consequently its efficiency ends up being low, the majority of the time. Furthermore, its applicability is low, because it cannot produce conjugated protein other than that of human origin utilizing the aforementioned human cell strain and due to other reasons.

A conjugated protein production method that addresses the above problems and can realize a long term and stable production of such proteins is therefore highly desired.

Accordingly, this invention aims to offer a novel human cell strain, wherein a transformed human cell strain is used to realize a long term and stable production of protein originated from a gene by means of gene transfection; a method of selecting the novel human cell strain; use of the novel human cell strain; a protein producing method utilizing the novel human cell strain; and a pharmaceutical composition utilizing the novel human cell strain.

In addition, there exist the following prior art literature related to the present invention in addition to the patent document 1 described above: Japanese Patent Laid-Open No. 2002-51780 (Patent document 1); JP-T 2001-500381 (Patent document 2); Japanese Patent laid-Open No. 8-163982 (Patent document 3); JP-T 2003-509025 (Patent document 4); Japanese Patent Laid-Open No. 5-310795; (Patent document 5); Japanese Patent Laid-Open No. 6-141882 (Patent document 6); JP-T 8-501695 (Patent document 7); Japanese Patent Laid-Open No. 6-78759 (Patent document 8); Japanese Patent Laid-Open No. 2003-274963 (Patent document 9); Japanese Patent Laid-Open No. 2002-58476 (Patent document 10); JP-T 2000-506379 (Patent document 11). However, none of these prior art disclosures achieve the above-mentioned objective of this invention.

SUMMARY OF THE INVENTION

A novel human cell strain enabling the continuous production of a desired protein with high efficiency, having a novel human cell strain established by transforming a human cell strain whose total intracellular protein weight is 0.1 to 1 mg per 1,000,000 cells; with the novel human cell strain being further characterized in that after a gene encoding a desired protein is transfected into it, the transfected cell is subsequently cultured.

It is embodied in another mode of the invention a novel human cell strain, enabling the continuous production of a desired protein at a yield of 1 ng-10 μg/day per 1,000,000 cells at least over a 2-month period, having a novel human cell strain established by transforming a specific human cell strain; with the novel human cell strain being further characterized in that after a gene encoding a desired protein is transfected into it, the transfected cell is subsequently cultured in a serum free medium.

It is embodied in a still further mode of the invention a method for selecting a novel human cell strain for producing a desired protein, including the steps of (a) selecting a human cell strain with a total intracellular protein of on or about 0.1-1 mg per 1,000,000 cell; and (b) choosing, out of human cell strains with a total intracellular protein of on or about 0.1-1.0 mg per 1.000,000 cells, cell clones which have a doubling time of 18 to 24 hours and which have a 90% rate of cloning by limiting dilution method; and mutating the cell clones with carcinogens; and selecting cells out of the mutated cells, which have a doubling time of 18 to 24 hours and a 90% rate of cloning by limiting dilution method, to be the novel human cell strain.

BRIEF DESCRIPTION OF THE DRAWINGS

FIG. 2A is a graph showing the cell proliferation (left) and FIG. 2B is a graph showing the cell viability (right) of the SC-01MFP in a serum free medium, in which the heavy chain protein of human antibody is expressed.

DETAILED DESCRIPTION OF THE PREFERRED EMBODIMENT

Figures 1A, 1B:
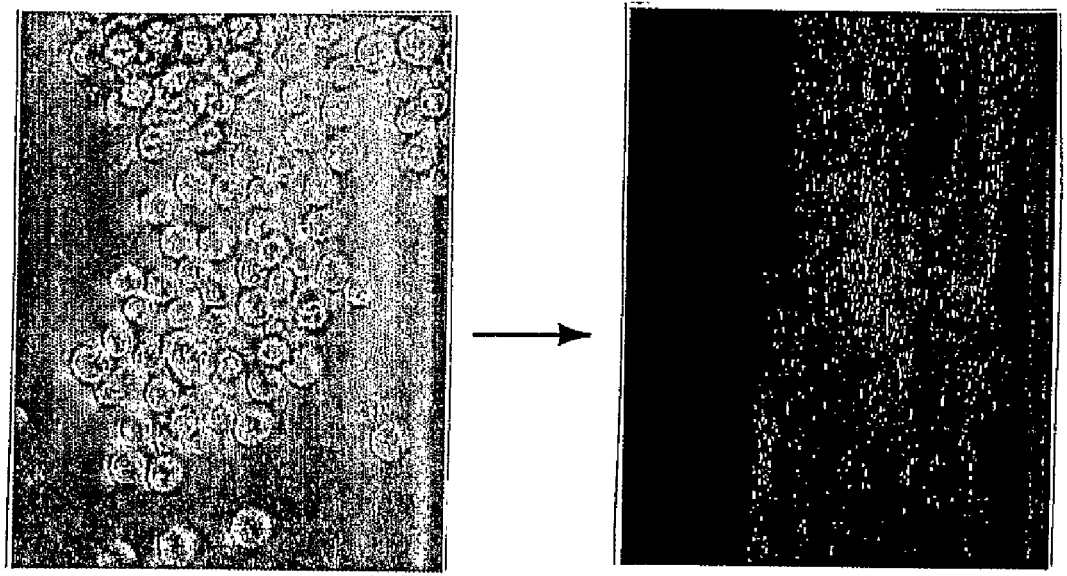
FIG. 1A is a picture by a transmission microscope (left) and FIG. 1B is a picture by an epi-illumination inverted microscope (right), which show the SC-01MFP cell strains of this invention, in which jellyfish GFP is expressed.

The inventors of this invention extensively researched how to select a human cell strain, which is transformed and subjected to medium exchanges to replicate infinitely, thereby allowing a long term stable protein production. The inventors then succeeded in selecting cell strains that exhibit the several cell characteristics described below and that withstand gene transfection. Subsequently, they studied the genes to be transfected and the medium components for culturing the cell, and established a serum-free cell culture technology. Finally, they completed a protein production technology that employs human cell strains.

More specifically, given that producing various proteins was the objective, upon selecting and identifying the human cell strains of this invention, a cell strain that had a high protein production rate by itself was selected from the cell strains originating from various human organs. Subsequently, the cell strain for protein production was subjected to the transfection of an exogenous gene and culturing procedures for expression. Then, the clones that proliferated with high efficiency from the state of being a single cell in a cultivation medium, were selected, considering the difficulties that arise against the survival and proliferation of the cell. In the embodiments of this invention, the cells having a doubling time of 18 to 24 hours and an over 90% rate of cloning efficiency by limiting dilution meet this criterion.

Moreover, in the embodiments of this invention, for producing proteins in mammalian cells, a vector containing a cytomegalovirus promoter, a G418 drug resistant gene, and a gene encoding human antibody heavy chain was constructed, and this vector was transfected with candidates of human cells for producing proteins, then their efficiencies were examined by measure of the expressed proteins. After these steps, the novel human cell strains SC-01MFP and SC-02MFP cells, having a stable and continuous production of the transfected gene-derived proteins with a high efficiency rate of 1 ng-10 µg/1,000,000 cels per day over a incubation period of at least two months or more, preferably over a half-year, and even more preferably over one year, were isolated and established.

The SC-01MFP and SC-02MFP cells pertinent to this embodiment can synthesize and produce proteins of other living species besides proteins of human origin.

The resulting present invention is described in detail with reference to the embodiments and examples, as follows.

The present invention is a method for producing proteins by a human cell stain, and the synthesized proteins depend largely on the characteristics of the human cell strain used. Accordingly, the inventors of this invention acquired a mutated strain, by isolating and selecting a human cell strain from various kinds of human sources, that allows a long term stable protein production, as described below.

The human cell strains prepared for protein production of the invention are four types of human hemocyte cell strains (human leukemiaT-cell strain PEER, human leukemia cell strain SK-729-2, human myeloma cell strain KMS-12BM, RPM18226) and four types of cancer cell strains (human stomach cancer cell strain TMK-1, human lung cancer cell strain A549, human breast cancer cell strain MCF-7, human lung cancer cell strainPC-8). For the lymphocyte floating cells among these cells, a RPMI1640 medium was used as the basic synthetic medium. Since cancer cells are adherent cells, an ERDF medium was used. As a growth factor, fetal bovine serum (FBS) was used.

First, the total weight of intracellular proteins was set as a criterion for selecting a human cell strain for protein production. It is based on the knowledge of the inventors that larger the total weight of intracellular protein of cells, higher the yield of the protein production when a foreign gene is transfected. Therefore, having a total intracellular protein weight of 0.1-1 mg per 1,000,000 cells was set as a criterion, and the human cell strains that meet the criterion were selected.

Next, the proliferation characteristics and cloning efficiencies of the cells were set as selection criteria. It is based on the knowledge of the inventors that the cells that succeed in gene transfection must be multiplied from the state of a single cell at the initial culturing stage, and that they must multiply while resisting physical burdens subjected to the cell due to the gene transfection procedure. In this invention, an extremely high criterion of selecting a cell strain with a cloning rate of over 90% with a doubling time of 18-24 hours was applied.

These evaluation and fractionation were performed by cell cloning using limiting dilution and a cell function analysis technique using a flow cytometer.

The variant cells obtained as described were induced to mutate in a medium in which nitrosoguanidine, a carcinogenic substance, had been added. Subsequently, clones with high proliferation characteristics were cloned again by limiting dilution, and the ones with a cloning rate of over 90% were selected under the same conditions used above.

On the other hand, in order to use protein production of the human cell strain selected as described above, as a means to produce medicine and food material, it is difficult to separate/refine only a target protein, since foreign proteins and proteins with unknown components are mixed in the production using a medium containing fetal bovine serum, etc. Moreover, in the case of a highly concentrated culture, an inhibitory growth factor of serum origin may act, thus a serum-free culture is essential. Therefore, in order to enable a serum-free culture for a human cell strain for protein production, such a cell strain was sought for selection. For this type of example, insulin, transferrin, ethanolamine, and sodium selenite were used as growth factors.

Next, after forming a vector that recombined the G418 drug resistance gene and the heavy chain gene of a human antibody, which are genes for producing proteins in mammalian cells and promoters of cytomegalovirus origin, it was introduced and expressed in human cell candidates for protein production, and then their efficiencies were examined.

In this way, continuous protein expression of more than a two month period, preferably a stable production yield of protein over a half-year, or even more preferably over one year was set as the criteria, and the transformed human cell strain that met the criteria was established as human cell strain for protein production. The cell strain established from the RPM18226 cell strain of human myeloma origin was named as SC-01MFP (which is deposited at an International Patent Organism Depository, National Institute of Advanced Industrial Science and Technology, located at Tsukuba Central 6, 1-1, Higashi 1-chome, Tsukuba-shi, Ibaraki-ken 305-8566, Japan; on Jul. 28, 2004 for all designated states with Accession Number FERM BP-10077), and the one established from the KMS-12BM cell strain of human myeloma origin was named as SC-02MFP (which is deposited at an International Patent Organism Depository, National Institute of Advanced Industrial Science and Technology, located at Tsukuba Central 6, 1-1, Higashi 1-chome, Tsukuba-shi, Ibaraki-ken 305-8566, Japan; on Jul. 28, 2004 for all designated states with Accession Number FERM BP-10078).

This invention is related to the novel human cell strain selected as described above, the method for selecting this novel human cell strain, the use of the novel human cell strain, its protein producing and refining methods, and the pharmaceutical compositions utilizing the above-mentioned protein.

EXAMPLES

Next, examples of selecting novel human cell strains according to the embodiments of this invention and their results, examples of protein production employing the above-mentioned novel human cell strains, and other examples are explained. However, it is to be understood that they are merely representative examples, thus not limiting the scope of this invention.

Example 1

Production of Human Antibody Heavy Chain Protein Using the SC-01MFP Cell Strain

The cell concentration of the SC-01MFP cell strain was prepared to $1\times10^7$ cells/ml with a phosphate buffered saline (PBS). 500 µl of this cell suspension was added to a sample tube, and 1 µl (final concentration of 1 µg/ml) of a recombinant gene vector containing a cytomegalovirus promoter, a G418 drug resistant gene, and a gene encoding human antibody heavy chain was added. This [suspension] was transferred to 0.4 cm cuvettes for a Gene Pulsar, transgenic device (using in vivo electroporation). The cuvettes were inserted into the electrode of the Gene Pulsar, the voltage was set at 0.3 kV (0.875 kV/cm), then applied at 300 µF.

Next, it was transferred to a RPM11640 medium, and let stand for 5 minutes in a centrifuge tube. Then this centrifuge tube was centrifuged for 5 minutes at 400×g. The centrifuged supernatant was discarded, and after being suspended with 5 ml of 15% FBS-RPMI medium, it was dispensed into a 96 well culture plate at 100l/well. 2-4 days later, GENETICIN; antibiotic G-418 sulfate (final concentration of 2 µg/ml) was added, and selective culturing, where the cells other than the gene-transfected cells were terminated, was carried out.

For several weeks, the medium was changed continuously with fresh medium containing GENETICIN. Since cell proliferation was confirmed in several weeks (2-4 weeks), the protein weight of this antibody heavy chain (γ chain) was measured using an enzyme antibody technique. Table 1 shows this result. After transfecting the gene encoding antibody heavy chain protein into the SC-01MFP cell strain, using the method in this example, starting from the 40th day post transfection for over a one year period, it maintained continuously a production yield of approx. 1-2 µg/ml/$10^7$ cells, while being incubated.

Each clone of Table 1, showing the production yield after several days of incubation following the gene transfection, respectively, is an example of representative protein expression. The SC-01MFP cell strain without the gene transfection did not produce antibody heavy chain proteins. Therefore, it can be concluded that any clones described in this data are expressed by the transfected gene.

Given that at least two months or more, preferably a half year or more, and even more preferably over one year of stable protein production has been sought for a stable industrial level production, the SC-01MFP cell strain of this example meets this criteria, thereby confirming the achievement of one objective of this invention.

TABLE 1

| Productivity of Antibody Heavy Chain Protein using the SC-01MFP cell strain | | | | |
|---|---|---|---|---|
| | Productivity (µg/ml) Culture days | | | |
| Clone No. | 40 | 120 | 200 | 360 |
| Clone 1 | 0.798 | 1.367 | 1.952 | 1.932 |
| Clone 2 | 0.487 | 1.321 | 1.895 | 1.914 |

Example 2

Production of Human Interleukin 1α (IL-1) Protein Using the SC-01MFP Cell Strain The cell concentration of the SC-01MFP cell strain was prepared to $1\times10^7$ cells/ml with a saline solution, phosphate buffered saline (PBS). 500 µl of this cell suspension was added to a sample tube, and 1 µl (final concentration of 3 µg/ml) of a recombinant gene vector containing a cytomegalovirus promoter, and a gene encoding human IL-1 was added. This [suspension] was transferred to 0.4 cm cuvettes for a Gene Pulsar, transgenic device (using in vivo electroporation). The cuvettes were inserted into the electrode of the gene pulsar, where the voltage was set at 0.3 kV (0.875 kV/cm), then applied at 300 µF.

Next, it was transferred to a RPMI 1640 medium, and left alone for 5 minutes in a centrifuge tube. Then this centrifuge tube was centrifuged for 5 minutes at 400×g. The centrifuged supernatant was discarded, and after being suspended with 5 ml of 15% FBS-RPMI medium, it was dispensed into a 96 well culture plate at 100 µl/well. 2-4 days later, GENETICIN; antibiotic G-418 sulfate (final concentration of 2 µg/ml) was added, and selective culturing, where the cells other than the gene-transfected cells were terminated, was carried out.

For several weeks, the medium was changed continuously with fresh medium containing GENETICIN. Since cell proliferation was confirmed in several weeks (2-4 weeks), this IL-1 protein weight was verified using an IL-1 using a specific enzyme antibody technique. Table 2 shows this result. Each clone of Table 2, showing the production yield after over 120 days following the gene transfection, respectively, is an example of representative protein expression. The SC-01MFP cell strains without the gene transfection did not produce human interleukin 1α (IL-1) proteins. Therefore, it can be concluded that any clones described in this data are expressed by the gene transfection.

Also, a composition comprising this human interleukin 1α, a part thereof and physiologically acceptable carriers is one embodiment of a pharmaceutical composition according to this invention. However, the pharmaceutical composition of this invention is not limited to the one utilizing this human interleukin 1α.

TABLE 2

Human Interleukin 1α Protein Production Using SC-01MFP Cell Strain

| Clone No. | Productivity (µg/ml) |
|---|---|
| Clone 1 | 0.116-0.203 |
| Clone 2 | 0.145-0.259 |
| Clone 3 | 0.123-0.285 |

Example 3

Production of Jellyfish GFP Fluorescent Dye Using the SC-01MFP Cell Strain

The cell concentration of the SC-01MFP cell strain was prepared to 1×10^7 cells/ml with a phosphate buffered saline (PBS). 500 µl of this cell suspension was added to a sample tube, and 1 µl (final concentration of 3 µg/ml) of a recombinant gene vector containing a cytomegalovirus promoter and a gene encoding jellyfish GFP (Green Fluorescent Protein) was added. This [suspension] was transferred to 0.4 cm cuvettes for a Gene Pulsar, transgenic device (using in vivo electroporation). The cuvettes were inserted into the electrode of the Gene Pulsar, the voltage was set at 0.3 kV (0.875 kV/cm), then applied at 300 µF.

Next, it was transferred to a RPMI 1640 medium, and let stand for 5 minutes in a centrifuge tube. Then this centrifuge tube was centrifuged for 5 minutes at 400×g. The centrifuged supernatant was discarded, and after being suspended with 5 ml of 15% FBS-RPMI medium, it was dispensed into a 96 well culture plate at 100 µl/well. 2-4 days later, GENETICIN; antibiotic G-418 sulfate (final concentration of 2 µg/ml) was added, and selective culturing, where the cells other than the gene-transfected cells were terminated, was carried out.

For several weeks, the medium was changed continuously with fresh medium containing GENETICIN. Since cell proliferation was recognized in several weeks (2-4 weeks), the expression of the GFP was measured with excitation of the green fluorescent by epi-illumination inverted microscope to confirm the production of the protein. FIG. 1B shows this result. The data of FIGS. 1A and 1B, showing an image of clones in which the GFP was expressed and for which over 90 days has passed since the gene transfection, is an example of representative clones that expressed proteins.

As shown in the right picture, the GFP expressed cells emit fluorescent light by fluorescence excitation using the fluorescence microscope. The SC-01MFP cell strains without the gene transfection do not produce GFP protein. Therefore, it could be concluded that any clones described in this data are expressed by the gene transfection.

Example 4

Production of Heavy Chain Protein of Human Antibody Using the SC-02MFP Cell Strain The cell concentration of the SC-02MFP cell strain was prepared to 1×10^7 cells/ml with a saline solution, phosphate buffered saline (PBS). 500 µl of this cell suspension was added to a sample tube, and 1 µl (final concentration of 1 µg/ml) of a recombinant gene vector containing a cytomegalovirus promoter, a G418 drug resistance gene, and a gene encoding human antibody heavy chain was added. This [suspension] was transferred to 0.4 cm cuvettes for a Gene Pulsar, transgenic device (using in vivo electroporation). The cuvettes were inserted into the electrode of the Gene Pulsar, voltage was set at 0.4 kV (1.0 kV/cm), then applied at 300 µF.

Next, it was transferred to a RPMI1640 medium, and left alone for 5 minutes in a centrifuge tube. Then this centrifuge tube was centrifuged for 5 minutes at 400×g. The centrifuged supernatant was discarded, and after being suspended with 5 ml of 15% FBS-RPMI medium, it was dispensed into a 96 well culture plate at 100 µl/well. 2-4 days later, GENETICTN; antibiotic G-418 sulfate (final concentration of 2 µg/ml) was added, and selective culturing, where the cells other than the gene-transfected cells were terminated, was carried out.

For several weeks, the medium was changed continuously with fresh medium containing GENETICIN. Since cell proliferation was recognized in several weeks (2-4 weeks), this antibiotic heavy chain (γ chain) protein weight was measured using an enzyme antibody technique. Table 3 shows this result.

TABLE 3

Productivity of Heavy Chain Protein of Antibody using SC-02MFP Cell Strain

| | Productivity (µg/ml) Culture days | | | |
|---|---|---|---|---|
| Clone No. | 40 | 80 | 140 | 210 |
| Clone 1 | 1.834 | 1.057 | 1.444 | 0.839 |
| Clone 2 | 1.803 | 1.200 | 1.669 | 0.671 |

Example 5

Serum-Free Culture of the SC-01MFP Cell Strain, Wherein Heavy Chain Proteins of Human Antibody have been Expressed The cell concentration of the cell clones, where the SC-01MFP cell strain has been transfected with a gene encoding a human antibody heavy protein and the protein has been expressed for a long-term, is prepared to 1×10^5 cells/ml. Next, it was incubated in a medium ITES-ERDF, where 10 µg/ml of insulin, 20 µg/ml of transferrin, 20 µM of ethanolamine, and 25 nM of sodium selenite are added to a minimal essential medium ERDF (Kyokuto Pharmaceutical) as final concentration, or otherwise incubated only in a minimal essential medium ERDF. As shown in FIGS. 2A and 2B, cell proliferations of said clone, incubated in only ERDF medium or ITES-ERDF medium, are confirmed as equivalent to or greater than that with the medium ERDR containing fetal bovine serum (FBS), which is ordinarily used for cell cultivation.

Example 6

Large-Scale and High-Density Culture of the SC-01MFP Cell Strain, Wherein Heavy Chain Proteins of Human Antibody have been Expressed The cell concentration of the cell clones, where the SC-01MFP cell strain has been transfected with a gene encoding a human antibody heavy protein and the protein has been expressed for a long period of time, is prepared to $0.2\times10^7$ cells/ml to $1\times10^7$ cells/ml. Next, it was inoculated to a hollow fiber cartridge (400-011, Spectrum Inc, US) using a medium ITES-ERDF, where either 10% of fetal bovine serum is added, or 10 µg/ml of insulin, 20 µg/ml of transferrin, 20 µM of ethanolamine, and 25 nM of sodium selenite are added to a minimal essential medium ERDF (Kyokuto Pharmaceutical) as final concentration; or otherwise only using a minimal essential medium ERDF. After the inoculation, it was incubated using a large-scale and high-density culturing unit (US, Spectrum Inc, CellMax system).

Figure 3:
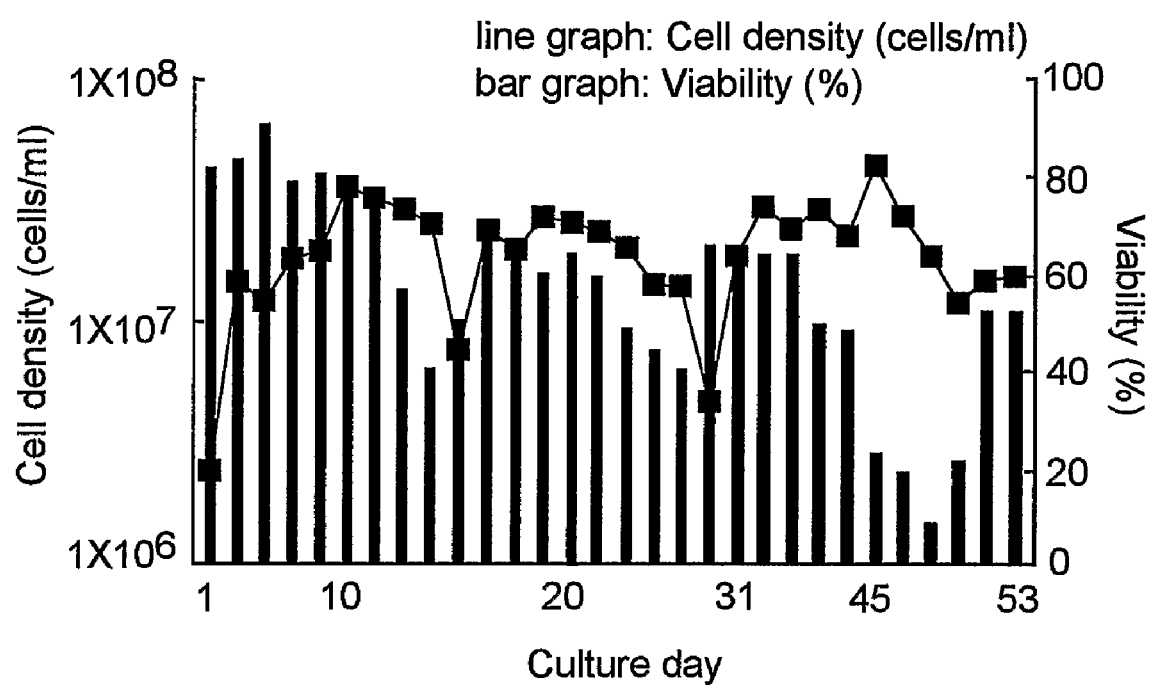
FIG. 3 is a graph showing the result of high-scale and high-density culturing of a gene transfected human cell strain.

As shown in FIG. 3, the SC-01MFP cell strain, expressing heavy chain proteins of human antibody, are mass cultured ($10^7$ to $10^8$/ml). The concentration of produced protein after this large scale culturing was at a level of 10 µg to 1 mg.

According to the compositions described above, the following effects can be obtained.

In other words, the production of conjugated proteins such as glycoprotein that regulate the physiology of the human body, and high-function proteins that possess a number of functions within a molecule, is essential for functional foods and advanced medical fields. Up to now, mainly microorganisms were used; however, with that method it is difficult to produce conjugated proteins. In the cases of using yeasts and advanced cells such as hamster cells, conjugated proteins can be produced. However, the proteins that are obtained have glycosylation that is specific to the cell involved in the production. Thus they are not the conjugated proteins with a desired physiology or molecular structure.

Such problems in principle can be solved by employing human cells for production. However, although it is possible to produce conjugated proteins using human cells in a transient fashion, it has been impossible to produce them in a long-term stable condition, necessary for industrial production levels.

Within the human body, proteins with various physiologies are circulating, and human cells generate these proteins. This is because human cells possess the mechanisms to generate such proteins, which microorganisms do not posses. However, human cells recently separated from the human body have limited life. Therefore, even when a production target gene is successfully transfected, it is well known that stability in production and long-term productivity, which are the criteria of industrial production, cannot be maintained.

The present invention aimed to obtain human cell strains for the industrial production of conjugated proteins that include high-function proteins (possessing complex functions resulting from molecular-design), sugar chains, and lipids, such as bioproteins, in order to establish the production method thereof. Establishing this technology enables its application to the production of pharmaceuticals, food ingredients, and chemical materials.

This invention can be used for the production of protein medicines as bio-pharmaceuticals; the manufacturing of functional ingredients that can be used for functional foods; the production of protein as raw materials for cosmetics including biological components; the analyses of various diseases and intercellular physiologic activities; and research regarding the expression of protein from genomic information, etc. However, it is to be understood that these applicable areas are merely exemplary, and the invention can be applied to any fields related to the acquiring of proteins. Thus, its technically applicable areas are not limited by those mentioned in this specification.

Furthermore, the foregoing description of the embodiments of this invention has been presented for the purposes of illustration and description. It is not intended to be exhaustive or to limit the embodiments of the invention to the form disclosed; obviously, many modifications and variations are possible. Such modifications and variations that may be apparent to a person skilled in the art are intended to be included within the scope of this invention as defined by the accompanying claims.

The invention claimed is:

1. A human cell strain SC-02MFP deposited as Accession Number FERM BP-10078.

2. A human cell strain SC-01MFP deposited as Accession Number FERM BP-10077.

3. A human cell strain capable of continuous production of a protein from an exogenous gene at a yield of 1 ng to 10 µg/day per 1,000,000 cells at least over a 2-month period, wherein said human cell strain is SC-01MFP (Accession No. FERM BP-10077) or SC-02MFP (Accession No. FERM BP-10078).

* * * * *